(12) United States Patent
Shigeta et al.

(10) Patent No.: US 11,459,410 B2
(45) Date of Patent: Oct. 4, 2022

(54) HIGH-PURITY AMPHIPATHIC ARYLSULFONIC ACID AMINE SALT VINYL MONOMER AND COPOLYMER THEREOF

(71) Applicant: TOSOH FINECHEM CORPORATION, Shunan (JP)

(72) Inventors: Yusuke Shigeta, Shunan (JP); Shinji Ozoe, Shunan (JP); Akihiro Fuji, Shunan (JP)

(73) Assignee: TOSOH FINECHEM CORPORATION, Shunan (JP)

( * ) Notice: Subject to any disclaimer, the term of this patent is extended or adjusted under 35 U.S.C. 154(b) by 215 days.

(21) Appl. No.: 16/637,729

(22) PCT Filed: Aug. 6, 2018

(86) PCT No.: PCT/JP2018/029428
§ 371 (c)(1),
(2) Date: Feb. 7, 2020

(87) PCT Pub. No.: WO2019/031454
PCT Pub. Date: Feb. 14, 2019

(65) Prior Publication Data
US 2020/0172643 A1 Jun. 4, 2020

(30) Foreign Application Priority Data
Aug. 7, 2017 (JP) .............................. JP2017-152646

(51) Int. Cl.
| | |
|---|---|
| C08F 12/30 | (2006.01) |
| B01J 41/14 | (2006.01) |
| C07C 209/68 | (2006.01) |
| C07C 211/62 | (2006.01) |
| C07C 211/63 | (2006.01) |
| C07C 303/22 | (2006.01) |
| C07C 309/30 | (2006.01) |

(52) U.S. Cl.
CPC .............. *C08F 12/30* (2013.01); *B01J 41/14* (2013.01); *C07C 209/68* (2013.01); *C07C 211/62* (2013.01); *C07C 211/63* (2013.01); *C07C 303/22* (2013.01); *C07C 309/30* (2013.01); *C07C 2601/14* (2017.05)

(58) Field of Classification Search
CPC ... C07C 303/32; C07C 209/68; C07C 211/62; C07C 211/63; C07C 303/22; C07C 309/30; C07C 2601/14; B01J 41/14
See application file for complete search history.

(56) References Cited

U.S. PATENT DOCUMENTS

| | | | | |
|---|---|---|---|---|
| 2,753,251 A * | 7/1956 | Gerjovich | ............... | A01N 47/30 504/330 |
| 4,029,640 A * | 6/1977 | Hattori | ............... | C07C 303/32 525/340 |
| 4,061,669 A * | 12/1977 | Katsuragawa | ........ | C07C 309/00 562/87 |
| 4,115,436 A * | 9/1978 | Katsuragawa | ........ | C07C 303/32 562/84 |
| 4,954,654 A * | 9/1990 | Efner | ...................... | C07C 209/26 564/446 |
| 7,919,565 B2 * | 4/2011 | Willis | ................... | H01M 4/661 525/333.5 |
| 8,093,342 B2 | 1/2012 | Minami et al. | | |

FOREIGN PATENT DOCUMENTS

| | | | |
|---|---|---|---|
| JP | 47-17731 | | 9/1972 |
| JP | 48-65237 | | 9/1973 |
| JP | 4865237 | A * | 9/1973 |
| JP | 50-149642 | A | 11/1975 |
| JP | 51-26842 | A | 3/1976 |
| JP | 8-104787 | A | 4/1996 |
| JP | 2000-273119 | A | 10/2000 |
| JP | 2003-34676 | A | 2/2003 |
| JP | 2014-32952 | A | 2/2014 |

OTHER PUBLICATIONS

Y. Liu et al., Synthesis and characterization of poly(trialkylammonium styrenesulfonate) polymers, PMSE Preprints (2010) (Year: 2010).*
J. March, Advanced Organic Chemistry Reactions, Mechanismsand Structure 37-64 (3rd ed., 1985) (Year: 1985).*
International Union of Pure and Applied Chemistry, Compendium of Chemical Terminology, Gold Book (2012) (Year: 2012).*
CAS Abstract and Indexed Compounds, Y. Liu et al., PMSE Preprints (2010) (Year: 2010).*
V. Consolante et al., 5 Macromol. React. Eng., 575-586 (2011) (Year: 2011).*
K. Pollock et al., 50 Polymer Preprints, 542 (2009) (Year: 2009).*
Y. Liu et al., 50 Polymer, 6212-6217 (2009) (Year: 2009).*
K. Cavicchi et al., ACS Applied Materials & Interfaces, 518-526 (2012) (Year: 2012).*
E. Pitia et al., 52 Polymer, 297-306 (2011) (Year: 2011).*

(Continued)

*Primary Examiner* — Alexander R Pagano
(74) *Attorney, Agent, or Firm* — Seed IP Law Group LLP

(57) ABSTRACT

The present invention provides a high-purity arylsulfonic acid amine salt vinyl monomer which is an extremely industrially useful arylsulfonic acid monomer with excellent storage stability and amphiphilic solubility in both water and organic solvents, a simple and practical method for producing the same, a polyarylsulfonic acid amine salt which is a polymer thereof, and a method for producing the same. In the arylsulfonic acid amine salt vinyl monomer, a tertiary amine having 2 or 3 different substituents that each have 1 to 7 carbon atoms and also containing at least one or more of tertiary carbon or quaternary carbon or cyclic skeleton in the structure is applied to an amine moiety thereof, and in addition, a polyarylsulfonic acid amine salt having high purity in terms of sulfonation rate and polymerization conversion rate and a polymer thereof are used.

1 Claim, 2 Drawing Sheets

(56) References Cited

OTHER PUBLICATIONS

Consolante et al., "Nitroxide-Mediated Polymerization of an Organo-Soluble Protected Styrene Sulfonate: Development of Homo- and Random Copolymers," *Macromolecular Reaction Engineering* 5:575-586, 2011.

Liu et al., "Synthesis and Characterization of Poly(trialkylammonium styrenesulfonate) Polymers," *Proceedings Published by the American Chemical Society*, 2 pages, 2010.

Liu et al., "Synthesis of poly(trioctylammonium p-styrenesulfonate) homopolymers and block copolymers by RAFT polymerization," *Polymer* 50:6212-6217, 2009.

Saito et al., "Polymer Adsorption Revolution by Graft Polymerization," *Maruzen Publishing*, pp. 8-9, 2014, (w/ English translation—7 pages).

\* cited by examiner

CHEMICAL SHIFT
NMR CHART OF CHASS

CHEMICAL SHIFT
NMR CHART OF DIPEASS

HIGH-PURITY AMPHIPATHIC ARYLSULFONIC ACID AMINE SALT VINYL MONOMER AND COPOLYMER THEREOF

TECHNICAL FIELD

The present invention relates to a high-purity amphiphilic arylsulfonic acid amine salt vinyl monomer having excellent storage stability and a high-purity arylsulfonic acid amine salt polymer obtained by using the arylsulfonic acid amine salt vinyl monomer as a raw material.

BACKGROUND ART

Styrenesulfonic acid salts typified by sodium styrene sulfonate are functional monomers having surfactant activity and cation exchange capacity, and have been used in a wide range of industrial fields as a raw material monomer for producing reactive emulsifiers for emulsion polymerization and other uses such as aqueous rheology control agents, aqueous dispersants, aqueous detergents, aqueous antistatic agents, conductive polymer aqueous colloid dopants, and ion exchange membranes.

However, well-known sodium salts, potassium salts, ammonium salts, and lithium salts of styrenesulfonic acid have extremely high water solubility, and their use is limited to aqueous applications because of their poor oil solubility. For example, among various antistatic agents added to prevent static electricity of resins and elastomers, antistatic agents of anionic polymer type are considered to be optimal in view of long-term retention of antistatic properties and heat resistance. In practice, however, anionic polymers such as polystyrenesulfonic acid salts are extremely poorly compatible with resins and elastomers, and are at least difficult to use alone (for example, see Patent Document 1).

Patent Document 1 discloses antistatic agents for the inside of a polymer substance. However, most of the examples disclosed are insoluble or sparingly soluble in room temperature water or hot water, and although it purports that those can be made water-dispersible or water-soluble by utilizing the structure of the neutralized amine, there is no description on the specific amine structure.

Therefore, cationic polymers and nonionic polymers are typically used; however, since cationic polymers have poor heat resistance and contain a large amount of halogen, it is difficult to apply them to electronic component applications, and nonionic polymers have poor antistatic properties and heat resistance, which are problematic.

Meanwhile, even in aqueous applications, the above-described styrenesulfonic acid salts have limited use because they have poor oil solubility or contain a metal component. For example, in a case where styrenesulfonic acid salts are used as a reactive emulsifier for oil-in-water type emulsion polymerization, the upper limit of the amount added is about 5 wt % (weight %) with respect to the oil-soluble monomer such as a methacrylic acid ester or styrene that serves as a base of the emulsion. Specifically, it has been difficult to obtain stable emulsion particles because severe aggregation occurs during polymerization when the amount of styrenesulfonic acid salt added is increased to about 10 wt %, for example, with an aim to further improve the stability of the emulsion or increase the sulfonic acid concentration on the surface of the emulsion particles. It is considered that this is because almost all of the styrenesulfonic acid salt is present in the aqueous phase, and thus polymer having the styrene sulfonic acid salt as a main component is formed in the aqueous phase. Further, in the case of producing emulsions for paints and adhesives using styrenesulfonic acid alkali metal salt, the stability of emulsion is improved by the addition of styrenesulfonic acid alkali metal salt. However, since metal members such as nails are easily corroded due to the alkali metal, the amount added is greatly limited.

Further, cation exchange fibers and membranes have been produced by a method involving graft-polymerizing a radically polymerizable monomer on a surface of a base material such as fiber, membrane, or nonwoven fabric. Due to its excellent durability against acid-alkali, polyolefin is mainly used as the base material. However, even if a polyolefin having poor hydrophilicity is immersed in an aqueous solution of styrene sulfonate, the efficiency of graft polymerization is extremely low because the styrenesulfonic acid salt cannot contact the polyolefin at the molecular level. Therefore, as disclosed in Non-Patent Document 1, a method involving graft-polymerizing styrenesulfonic acid salt to hydrophilic nylon and a method involving graft-polymerizing oil-soluble glycidyl methacrylate to polyolefin and then introducing sulfonic acid groups thereto have been made. However, since cation exchange fibers and membranes obtained using a nylon base material and glycidyl methacrylate all contain hydrolyzable amide groups and ester groups, there is the problem of durability against acid-alkali.

Therefore, as a method for graft-polymerizing styrenesulfonic acid having excellent chemical stability to a base material such as polyolefin or polyether ether ketone having excellent chemical stability, for example, use of a styrenesulfonic acid ester as in Patent Document 2 has been actively studied. However, as disclosed in, for example, Patent Document 3 and Patent Document 4, styrenesulfonic acid ester is produced through a complicated process using sodium styrene sulfonate as a starting material, and thus is very expensive and difficult to purify by distillation, making it difficult to produce a high-purity product.

Furthermore, when using styrenesulfonic acid ester, after graft polymerization, a new process for hydrolyzing the sulfonic acid ester with an acid or alkali and converting it to sulfonic acid is required, which is not suitable for industrial production.

Meanwhile, a method of improving the oil solubility by using styrenesulfonic acid in the form of a salt with a hardly water-soluble organic amine is also known. For example, a styrenesulfonic acid amine salt using a long-chain alkylamine such as trioctylamine disclosed in Non-Patent Document 2 and Non-Patent Document 3 is soluble in an aromatic hydrocarbon such as toluene. However, due to the large number of methylene groups it has, functionality of the sulfonic acid per unit weight of the styrenesulfonic acid salt decreases and chain transfer reaction is likely to occur during graft-polymerization (leading to decrease in polymerization rate and degree of polymerization of graft polymer), which are problematic.

Further, in addition to the styrenesulfonic acid amine salts, polystyrenesulfonic acid amine salts have also been reported. For example, Patent Document 1 discloses that polystyrenesulfonic acid amine salt obtained by sulfonating polystyrene and then neutralizing the resultant with an amine having 8 or more carbon atoms has improved compatibility with the resin and is useful as an antistatic agent.

Patent Document 5 discloses that a composition including trilaurylamine sulfuric acid salt and polystyrenesulfonic acid trilaurylamine salt obtained by sulfonating polystyrene, as in Patent Document 1, and then neutralizing the resultant with trilaurylamine improves the antistatic properties at low humidity, which has been a conventional problem.

In Patent Document 6, a polystyrenesulfonic acid is neutralized with an organic amine, dissolved in an alcohol solvent, and then dried to obtain a polymer styrenesulfonic acid organic amine salt useful as antistatic agent application.

However, in Patent Document 1 and Patent Document 5, sufficient sulfonation, in terms of high-purity, is not carried out in the sulfonation step, and furthermore, in Patent Document 6, a complicated operation is required for efficient separation of the organic solvent in order to obtain a high-purity product. For this reason, a sufficient sulfonation rate has not yet been reached, and there remains the problem of a decrease in purity due to various impurities. Furthermore, since these polystyrenesulfonic acid amine salts are polymers, it has been difficult to use them as the above-described reactive emulsifier for emulsion polymerization or as a monomer for producing a cation exchange membrane.

PRIOR ART DOCUMENT

Patent Document

Patent Document 1: Japanese Patent Laid-Open No. S48-65237
Patent Document 2: Japanese Patent Laid-Open No. 2014-32952
Patent Document 3: U.S. Pat. No. 8,093,342
Patent Document 4: Japanese Patent Laid-Open No. 2003-34676
Patent Document 5: Japanese Patent Laid-Open No. H08-104787
Patent Document 6: Japanese Patent Laid-Open No. 2000-273119

Non-Patent Document

Non-Patent Document 1: by Shinichi Saito, "Polymer Adsorbent Revolution through Graft Polymerization", p. 9, published by Maruzen Publishing, 2014
Non-Patent Document 2: Macromolecular Reaction Engineering, vol. 5 (11), 575-586, 2011
Non-Patent Document 3: Polymer, vol. 50 (26), 6212-6217, 2009

SUMMARY OF THE INVENTION

Problems to be Solved by the Invention

As a result of investigations by the present inventors, it has been found that conventional styrenesulfonic acid amine salts having oil solubility are extremely poor in storage stability, that is, the purity is easily lowered due to natural polymerization. Further, while it is a merit that the conventional styrenesulfonic acid amine salts have oil solubility, there is a disadvantage that the use of styrenesulfonic acid salt is narrowed conversely because of its poor water solubility.

For example, if an emulsion for paints and adhesives can be produced using styrenesulfonic acid trioctylamine instead of styrenesulfonic acid alkali metal salt, it can be expected that an extremely stable emulsion without metal corrosiveness can be produced. However, as a result of investigations by the present inventors, it has been found that since styrenesulfonic acid trioctylamine has poor water solubility, emulsion polymerization is difficult to proceed.

The present invention has been made in view of the above-described background and problems, and an object thereof is to provide a high-purity arylsulfonic acid amine salt vinyl monomer which is an extremely industrially useful arylsulfonic acid vinyl monomer with excellent storage stability and amphiphilic solubility in both water and organic solvents, a simple and practical method for producing the same, and a high-purity polyarylsulfonic acid amine salt which is a polymer thereof and a method for producing the same.

Means for Solving the Problems

As a result of intensive studies to solve the above problems, the inventors of the present invention have found that with respect to arylsulfonic acid salts derived from a para-styrenesulfonic acid compound or an arylsulfonic acid compound represented by a specific formula (1) and an aryl sulfonimide compound represented by a specific formula (2), a salt of the arylsulfonic acid with a tertiary amine represented by a specific formula (3) exhibits unique properties such as excellent storage stability and good solubility in organic solvents and water, thereby completing the present invention.

Specifically, the present invention relates to an arylsulfonic acid amine salt that is a salt of:

an arylsulfonic acid represented by Formula (1):

[Formula 1]

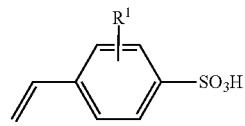

(1)

wherein $R^1$ is a hydrogen atom or an ethenyl group, or Formula (2):

[Formula 2]

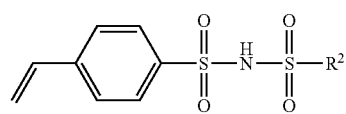

(2)

wherein $R^2$ represents an ethenyl group, a 4-ethenylphenyl group, fluorine, or a linear or branched alkyl group having 1 to 10 carbon atoms, a linear or branched alkenyl group having 2 to 10 carbon atoms, a linear or branched alkynyl group having 2 to 10 carbon atoms, or a cyclic alkyl group having 3 to 10 carbon atoms having an arbitrary number of substituents, and a tertiary amine represented by Formula (3):

[Formula 3]

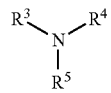

(3)

wherein structures of $R^3$, $R^4$, and $R^5$ are all different, or any two of $R^3$, $R^4$, and $R^5$ are the same, $R^3$, $R^4$, and $R^5$ are each independently a linear, branched, or cyclic saturated hydrocarbon group having 1 to 7 carbon atoms, an aryl group having 1 to 7 carbon atoms, or a hydroxyalkyl group having 1 to 7 carbon atoms, at least one of $R^3$, $R^4$, and $R^5$ has a tertiary or quaternary carbon, or has a ring structure, and the ring structure is an aryl group, a 5-membered or 6-membered cycloalkyl group, a 5-membered or 6-membered ring formed by any two of $R^3$, $R^4$, and $R^5$ bonding to each other, or a 5-membered or 6-membered ring formed by any two of $R^3$, $R^4$, and $R^5$ bonding to each other via an oxygen atom.

The present invention further relates to the above-described arylsulfonic acid amine salt, in which in Formula (3), the structures of $R^3$, $R^4$, and $R^5$ are all different, or any two of $R^3$, $R^4$, and $R^5$ are the same, $R^3$, $R^4$, and $R^5$ are each independently a linear, branched, or cyclic saturated hydrocarbon group having 1 to 7 carbon atoms, an aryl group having 1 to 7 carbon atoms, or a hydroxyalkyl group having 1 to 7 carbon atoms, at least one of $R^3$, $R^4$, and $R^5$ has a ring structure, and the ring structure is an aryl group, a 5-membered or 6-membered cycloalkyl group, a 5-membered or 6-membered ring formed by two of $R^3$, $R^4$, and $R^5$ bonding to each other, or a 5-membered or 6-membered ring formed by any two of $R^3$, $R^4$, and $R^5$ bonding to each other via an oxygen atom. Here, that at least one of $R^3$, $R^4$, and $R^5$ may have a ring structure means that both cases of having and not having a ring structure are included.

The present invention further relates to the above-described arylsulfonic acid amine salt, in which in Formula (1) or (2), $R^1$ is a hydrogen atom or an ethenyl group, and $R^2$ is an ethenyl group, a 4-ethenylphenyl group, or a trifluoromethyl group.

The present invention further relates to the above-mentioned arylsulfonic acid amine salt which is a salt of para-styrenesulfonic acid and N,N-dimethylcyclohexylamine.

The present invention further relates to a method for producing an arylsulfonic acid amine salt, the method comprising:

adding a mineral acid to a tertiary amine while cooling to obtain a salt, wherein the tertiary amine is represented by Formula (4):

[Formula 4]

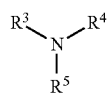

(4)

wherein $R^3$, $R^4$, and $R^5$ are as defined in Formula (3); and subsequently adding an arylsulfonic acid or a salt thereof to the obtained salt and reacting a resulting mixture, wherein the arylsulfonic acid is represented by Formula (5):

[Formula 5]

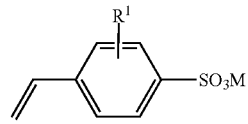

(5)

wherein $R^1$ is the same as defined in Formula (1), and M represents a hydrogen atom, an alkali metal ion, or an alkaline earth metal ion, or Formula (6):

[Formula 6]

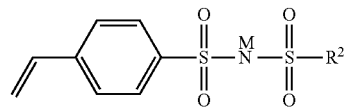

(6)

wherein $R^2$ is the same as defined in Formula (2), and M represents a hydrogen atom, an alkali metal ion, or an alkaline earth metal ion.

The present invention further relates to a method for producing an arylsulfonic acid amine salt, the method comprising:

mixing an aqueous solution or an organic solvent solution of an arylsulfonic acid with a tertiary amine, wherein the arylsulfonic acid is represented by Formula (7):

[Formula 7]

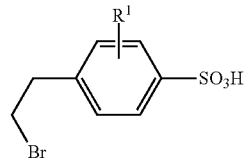

(7)

wherein $R^1$ is as defined in Formula (1), or Formula (8):

[Formula 8]

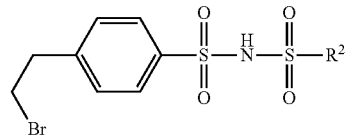

(8)

wherein $R^2$ is as defined in Formula (2), and the tertiary amine is represented by Formula (9):

[Formula 9]

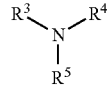

(9)

wherein $R^3$, $R^4$, and $R^5$ are as defined in Formula (3); and heating and reacting a resulting mixture.

The present invention further relates to a polymer of an arylsulfonic acid amine salt obtained by polymerizing the above-described arylsulfonic acid amine salt.

The present invention further relates to a method for producing a polymer of arylsulfonic acid amine salt, the method comprising:

dissolving the above-described arylsulfonic acid amine salt in an arbitrary solvent to obtain a mixture;

optionally adding and dissolving a molecular weight regulator and/or an emulsifier into the mixture;

adding a radical polymerization initiator into the mixture under a nitrogen atmosphere; and reacting the mixture with heating and stirring.

Advantageous Effects of the Invention

The arylsulfonic acid amine salt monomer of the present invention is an arylsulfonic acid compound having high purity, high storage stability, and amphiphilic properties, and is applicable not only to applications that requires lipophilicity, which was difficult to be obtained with conventional arylsulfonic acid salt monomers, such as prevention of static electricity of resins and rubbers and graft polymerization to polyolefins, but also to applications that require a certain degree of water solubility, which was difficult to be obtained with conventional arylsulfonic acid amine salt monomers, such as reactive emulsifiers for emulsion polymerization.

MODE FOR CARRYING OUT THE INVENTION

Figure 1:
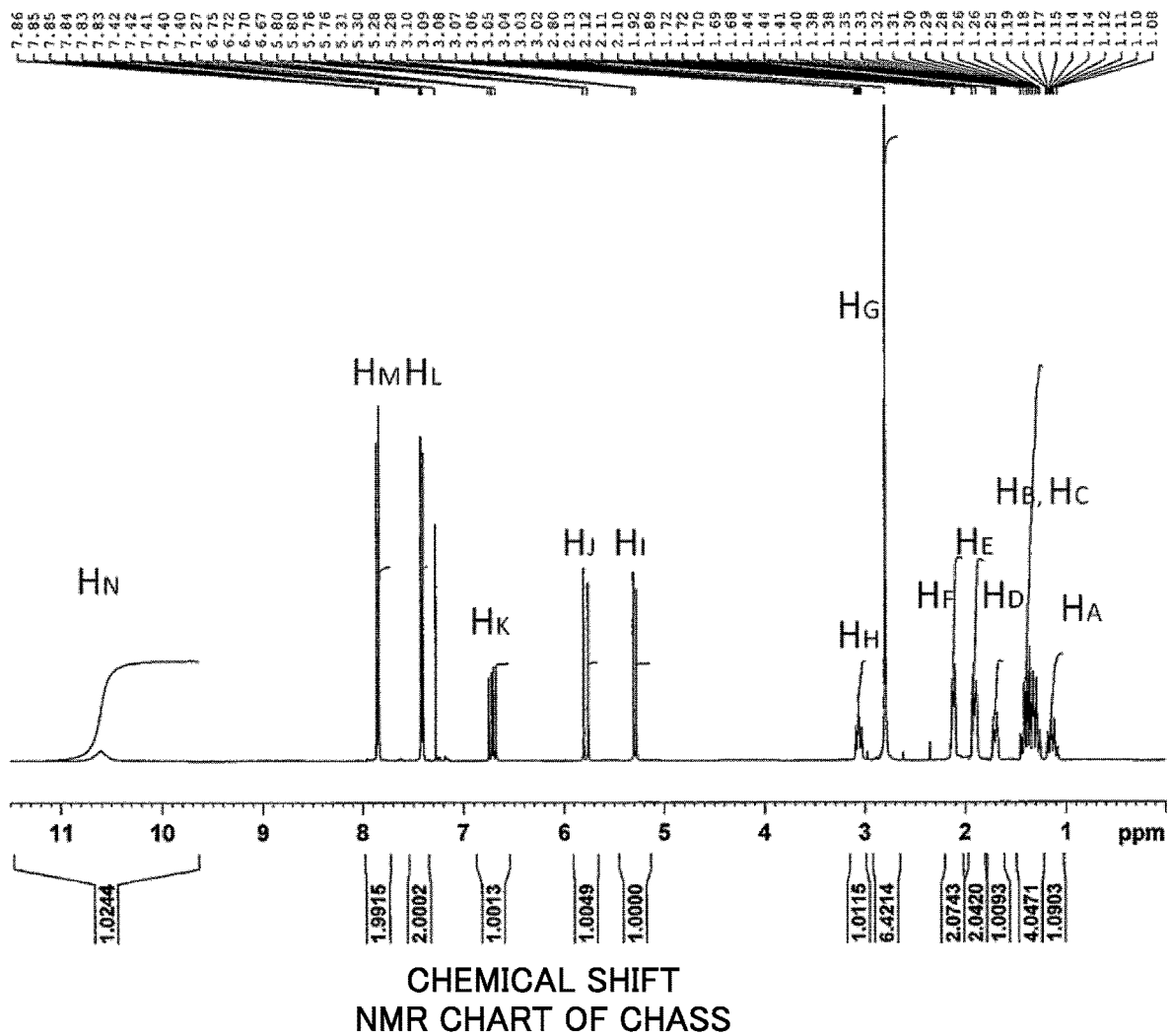
FIG. 1 is a proton NMR spectrum of parastyrenesulfonic acid N,N-dimethylcyclohexylamine salt (abbreviated as CHASS) obtained in Example 1, in which protons $H_A$, $H_B$, $H_C$, $H_D$, $H_F$, $H_G$, $H_H$, $H_I$, $H_J$, $H_K$, $H_L$, $H_M$, and $H_N$ in the figure correspond to protons $H_A$, $H_B$, $H_C$, $H_D$, $H_F$, $H_G$, $H_H$, $H_I$, $H_J$, $H_K$, $H_L$, $H_M$, and $H_N$ in FIG. 2, respectively.
Figure 2:
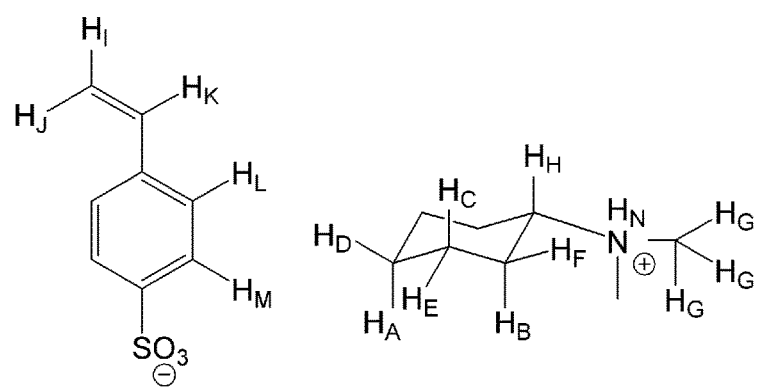
FIG. 2 is a structural formula identified from the proton NMR spectrum of parastyrenesulfonic acid N,N-dimethylcyclohexylamine salt obtained in Example 1.
Figure 3:
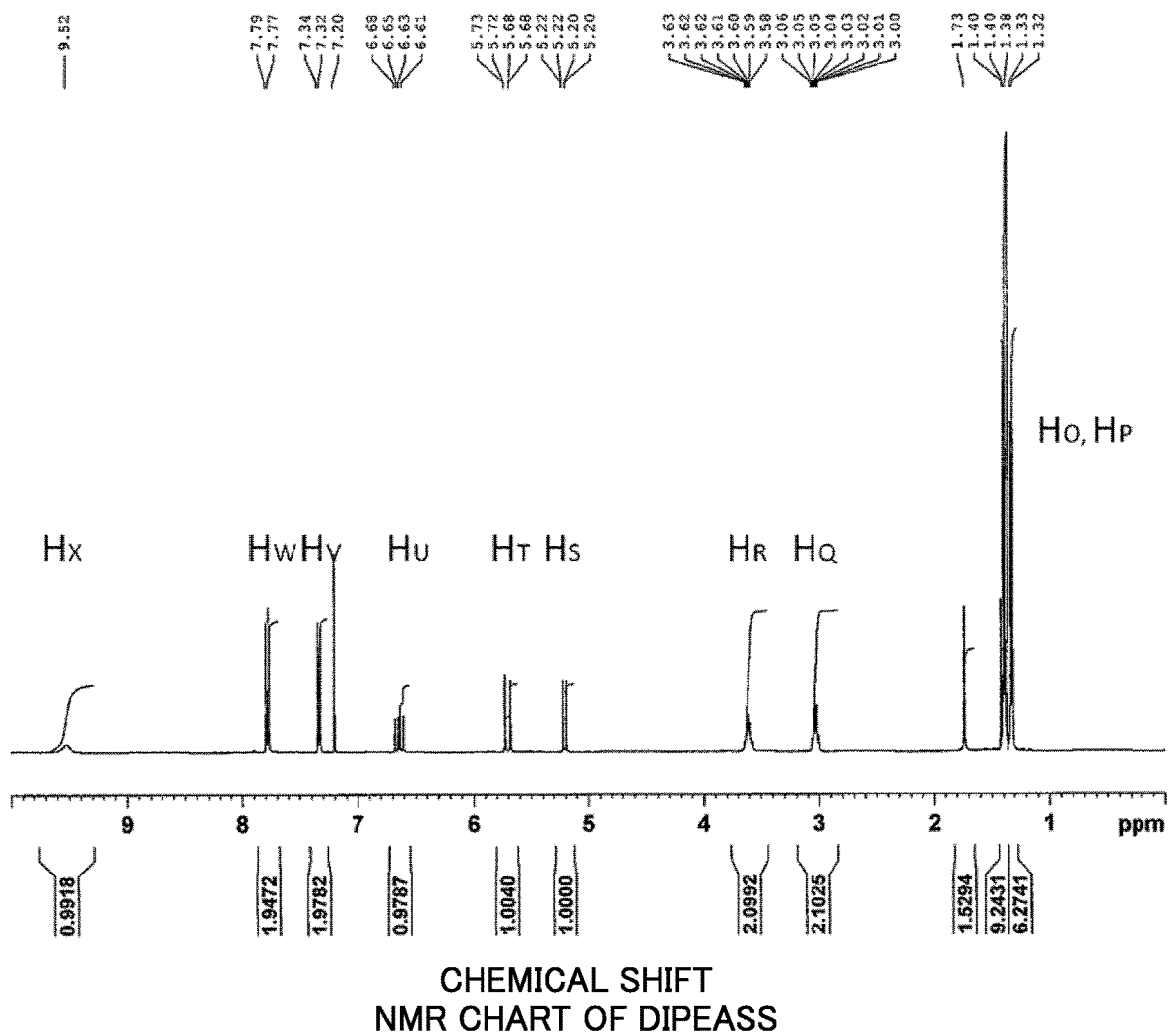
FIG. 3 is a proton NMR spectrum of N,N-diisopropylethylamine salt of parastyrenesulfonic acid (abbreviated as DIPEASS) obtained in Example 3, in which protons $H_O$, $H_P$, $H_Q$, $H_R$, $H_S$, $H_T$, $H_U$, $H_V$, $H_W$, and $H_X$ correspond $H_O$, $H_P$, $H_Q$, $H_R$, $H_S$, $H_T$, $H_U$, $H_V$, $H_W$, and $H_X$ in FIG. 4, respectively.
Figure 4:
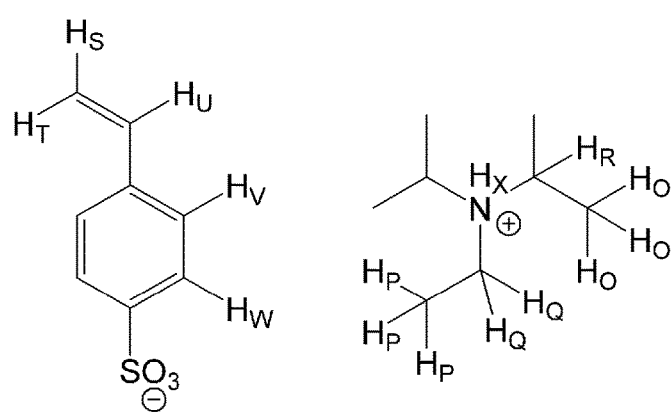
FIG. 4 is a structural formula identified from the proton NMR spectrum of N,N-diisopropylethylamine salt of parastyrenesulfonic acid obtained in Example 3.

The present invention relates to arylsulfonic acid salts derived from a parastyrenesulfonic acid compound or an arylsulfonic acid compound represented by a specific formula (1) and an aryl sulfonimide compound represented by a specific formula (2), and relates to a salt of the arylsulfonic acid with a tertiary amine represented by a specific Formula (3) and a polymer thereof.

Hereinafter, a mode for carrying out the present invention (hereinafter referred to as "the present embodiment") will be described in detail. In addition, the present invention is not limited to the present embodiment below. The present invention can be appropriately modified and implemented within the scope of the gist.

Arylsulfonic Acid Amine Salt

The arylsulfonic acid amine salt vinyl monomer of the present embodiment is an arylsulfonic acid amine salt which is a salt of an arylsulfonic acid represented by Formula (1) or Formula (2) and a tertiary amine represented by Formula (3) and is a polymer thereof.

[Formula 1]

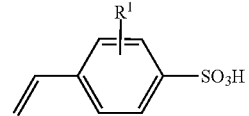

(1)

wherein $R^1$ represents a hydrogen atom or an ethenyl group,

[Formula 2]

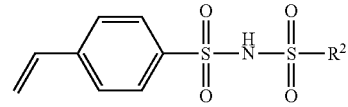

(2)

wherein $R^2$ represents an ethenyl group, a 4-ethenylphenyl group, fluorine, or a linear or branched alkyl group having 1 to 10 carbon atoms, a linear or branched alkenyl group having 2 to 10 carbon atoms, a linear or branched alkynyl group having 2 to 10 carbon atoms, or a cyclic alkyl having 3 to 10 carbon atoms having an arbitrary number of substituents,

[Formula 3]

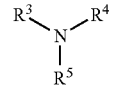

(3)

wherein structures of $R^3$, $R^4$, and $R^5$ are all different, or any two of $R^3$, $R^4$, and $R^5$ are the same, $R^3$, $R^4$, and $R^5$ are each independently a linear or branched saturated hydrocarbon group, an aryl group, or a hydroxyalkyl group having 1 to 7 carbon atoms, at least one of $R^3$, $R^4$, and $R^5$ has a tertiary or quaternary carbon or has a ring structure in the structure thereof, and the ring structure is an aryl group, a 5-membered or 6-membered cycloalkyl group, a 5-membered or 6-membered ring formed by any two of $R^3$, $R^4$, and $R^5$ bonding to each other, or a 5-membered or 6-membered ring formed by any two of $R^3$, $R^4$, and $R^5$ bonding to each other via an oxygen atom.

Specific examples of the arylsulfonic acid compound and the tertiary amine compound in the present embodiment will be described later.

Method for Producing Arylsulfonic Acid Amine Salt

A method for producing the arylsulfonic acid amine salt vinyl monomer of the present embodiment is not particularly limited. An exemplary method capable of producing the same is a method including placing a solution of an arylsulfonic acid metal salt in a reactor equipped with a stirrer, a cooling pipe, and a dropping pipe under nitrogen atmosphere, adding dropwise a solution of an inorganic acid salt of a tertiary amine thereto, and performing salt exchange in a homogeneous system or a two-phase system. In this method, a tertiary amine inorganic acid solution may be placed in the reactor, and then the arylsulfonic acid metal salt solution may be added dropwise.

The molar ratio of the arylsulfonic acid metal salt/tertiary amine inorganic acid salt at the time of placing is not particularly limited, but is preferably 0.5 to 4.0, and is particularly preferably 0.8 to 1.5 in view of removing raw materials or by-products.

In the above production method, examples of the metal for the arylsulfonic acid metal salt include alkali metals or alkaline earth metals such as sodium, potassium, lithium, calcium, and magnesium, and sodium is particularly desirable in view of availability and crystallization properties.

Although the inorganic acid in the tertiary amine inorganic acid salt is not particularly limited, examples thereof include hydrochloric acid, nitric acid, phosphoric acid, sulfuric acid, boric acid, hydrofluoric acid, hydrobromic acid, hydrocyanic acid, and hexafluorophosphoric acid, and the inorganic acid may be used regardless of its properties and may be in forms such as gas, aqueous solution, and organic solvent solution. Hydrochloric acid gas or aqueous hydrochloric acid solution is preferable in view of availability and ease of handling.

The reaction solvent for placing in the reactor and the solvent used for the dropping solution (dropping solvent) are not particularly limited as long the as the arylsulfonic acid alkali metal and the tertiary amine inorganic acid salt can be dissolved therein, and the reaction solvent and the dropping solvent may be the same as or different from each other.

Examples thereof include water or water-soluble solvents such as water, acetone, tetrahydrofuran, dioxane, methanol, ethanol, n-propanol, isopropanol, methoxyethanol, ethoxyethanol, butanol, ethylene glycol, propylene glycol, glycerin, dimethyl sulfoxide, dimethylformamide, and N-methylpyrrolidone, aliphatic hydrocarbons such as pentane, hexane, heptane, octane, nonane, decane, undecane, dodecane, tridecane, tetradecane, pentadecane, hexadecane, heptadecane, octadecane, cyclohexane, and methylcyclohexane, aromatic hydrocarbons such as benzene, toluene, o-xylene, m-xylene, and p-xylene, aliphatic halogen compounds such as methylene chloride, chloroform, carbon tetrachloride,1,2-dichloroethane, 1,1,1-trichloroethane, and 1,1,2-trichloroethane, ester solvents such as ethyl acetate and butyl acetate, ether solvents such as diethyl ether, methyl ethyl ether, and cyclopentyl methyl ether, and a mixture thereof.

The solvent for the arylsulfonic acid metal salt is preferably water or a mixed solution of water and a water-soluble solvent. The solvent for the amine inorganic acid salt varies depending on the properties of the amine, but water or water and water-soluble solvents, halogenated solvents such as chloroform and dichloromethane are preferable because the amine inorganic salt has high solubility therein and can be easily removed therefrom.

The concentration of the arylsulfonic acid amine salt is 5 wt % (weight %) to 79 wt % with respect to the total amount placed, and is preferably 10 wt % to 70 wt % in view of promoting the reaction and suppressing by-products.

The reaction temperature is preferably −20° C. to 50° C., and more preferably 0° C. to 30° C. in view of heat polymerization.

The arylsulfonic acid amine salt vinyl monomer obtained by the exemplified method can be separated and purified from the reaction solution after completion of the reaction by a conventional method such as filtration, extraction or crystallization. The method for separation and purification mainly depends on the material properties of the tertiary amine used. For example, in a case where the target product is isolated by extraction, a metal inorganic acid salt produced as a by-product, an unreacted arylsulfonic acid metal salt, and an amine inorganic acid salt are dissolved in the aqueous layer, and an arylsulfonic acid amine salt is dissolved in the organic layer in many cases.

Examples of the extraction solvent include single or mixed solvents of organic solvents such as: aromatic hydrocarbon solvents such as toluene and xylene; halogenated solvents such as chloroform, dichloromethane, 1,1,1-trichloroethane, and 1,1,2-trichloroethane; aliphatic hydrocarbon solvents such as hexane, cyclohexane, and methylcyclohexane; ester solvents such as ethyl acetate and butyl acetate; and ether solvents such as diethyl ether, methyl ethyl ether, and cyclopentyl methyl ether.

As another example of the method for producing the arylsulfonic acid amine salt vinyl monomer of the present embodiment, there is a method in which a dehalogenation reaction of haloethylarylsulfonic acid and neutralization of sulfonic acid occur simultaneously.

In the case of the parastyrenesulfonic acid amine salt as an example, first, a 4-(2-haloethyl)benzenesulfonic acid solution and a radical polymerization inhibitor are placed in a reactor equipped with a stirrer and a cooling pipe, followed by sufficiently deoxygenating the system, and after raising the temperature to a predetermined temperature, a tertiary amine or a solution thereof is continuously dropped into the mixture to cause vinylation reaction (dehalogenation) so as to produce the parastyrenesulfonic acid amine salt. Alternatively, a tertiary amine or a solution thereof and a polymerization inhibitor may be placed in a reactor, followed by sufficiently deoxygenating the system, and after raising the temperature to a predetermined temperature, the 4-(2-haloethyl)benzenesulfonic acid solution may be dropped continuously to cause vinylation reaction. Alternatively, a polymerization inhibitor and a part of the tertiary amine or a solution thereof may be placed in a reactor, followed by sufficiently deoxygenating the system, and after raising the temperature to a predetermined temperature, a 4-(2-haloethyl)benzenesulfonic acid solution and the remaining amine solutions may be dropped continuously to cause vinylation reaction.

Although the polymerization inhibitor that may be used in the production method of the present invention is not particularly limited, examples thereof include nitrous acid alkali metal salt, hydroquinone, methoxyhydroquinone, anthraquinone sulfonic acid salt, ammonium nitrosophenylhydroxylamine, N-nitrosophenylhydroxyamine aluminum salt, 2-t-butylhydroquinone, and 4-t-butylcatechol.

The amount of the polymerization inhibitor added is preferably 10 ppm to 1 wt % with respect to the arylsulfonic acid amine salt.

The reaction solvent for placing in the reactor and the solvent used for the dropping solution are not particularly limited as long as the haloethylarylsulfonic acid and the tertiary amine can be dissolved therein and the reaction is not affected by the solvents, and examples thereof include water or water-soluble solvents such as the water, acetone, tetrahydrofuran, dioxane, dimethyl sulfoxide, dimethylformamide, and N-methylpyrrolidone, aromatic hydrocarbons such as benzene, toluene, o-xylene, m-xylene, and p-xylene, and aliphatic halogen compounds such as methylene chloride, chloroform, carbon tetrachloride, and 1,2-dichloroethane. Water, methylene chloride, chloroform, carbon tetrachloride, 1,2-dichloroethane are preferred in view of ease of dehalogenation and substrate solubility.

Parastyrenesulfonic-acid amine salt precipitates by vinylation reaction and cooling of a reaction solution in the above-described production method. The crystals can be separated by a method such as centrifugal filtration to obtain a water-containing salt of parastyrenesulfonic acid amine salt. Thereafter, the moist content may be further reduced by solvent washing, vacuum drying, or other technique. Furthermore, in order to remove inorganic and organic impurities such as inorganic salts contained in divinylbenzenesulfonic acid salt, recrystallization purification or repulp purification may be performed using water, a mixed solvent of water and a water-soluble solvent, an arbitrary organic solvent, or the like.

Although the purification solution is not particularly limited, examples therefor include water-soluble solvents such as methanol, ethanol, isopropanol, n-propanol, butanol, acetone, tetrahydrofuran, and acetonitrile, linear aliphatic hydrocarbons such as pentane, hexane, cyclohexane, methylcyclohexane, heptane, octane, nonane, decane, undecane, dodecane, tridecane, tetradecane, pentadecane, hexadecane, heptadecane, and octadecane, and aromatic hydrocarbons such as benzene, toluene, o-xylene, m-xylene, and p-xylene, and aliphatic halogen compounds such as methylene chloride, chloroform, carbon tetrachloride, and 1,2-dichloroethane.

Arylsulfonic Acid

Specific examples of the arylsulfonic acid used for the present embodiment include parastyrenesulfonic acid, orthostyrenesulfonic acid, metastyrenesulfonic acid, orthodivinylbenzenesulfonic acid, metadivinylbenzenesulfonic acid, and paradivinylbenzenesulfonic acid represented by General Formula (1), but not particularly limited thereto as long as the arylsulfonic acid is a compound having one or two vinyl groups in an aromatic ring; specific examples of $R^2$ in Formula (2) include an ethenyl group, 4-ethenylphenyl group, a trifluoromethyl group, a methyl group, an ethyl group, a n-propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a cyclopropyl group, a cyclobutyl group, a cyclopentyl group, a cyclohexyl group, a methylcyclopropyl group, a 1-methylcyclobutyl group, a 2-methylcyclobutyl group, a 1-methylcyclopentyl group, a 2-methylcyclopentyl group, a 1-methylcyclohexyl group, a 2-methylcyclohexyl group, a 3-methylcyclohexyl group, a 1,1-dimethylcyclopropyl group, a 1,2-dimethylcyclopropyl group, a 1,1-dimethylcyclobutyl group, a 1,2-dimethylcyclobutyl group, a 1,3-dimethylcyclobutyl group, and a 2,2-dimethylcyclobutyl group, and the arylsulfonic acid may have a substituent at any position as long as the reaction is not inhibited. Among them, parastyrenesulfonic acid, paradivinylbenzenesulfonic acid, and metadivinylbenzenesulfonic acid are preferable of those represented by General Formula (1), and an ethenyl group, a 4-ethenylphenyl group, and a trifluoromethyl group are preferable as $R^2$ in General Formula (2), in view of availability of raw materials.

Tertiary Amine

Although the tertiary amines of General Formula (3) used in the present embodiment have been described above, it is preferable that at least one of $R^3$, $R^4$, and $R^5$ be a 5-membered or 6-membered cycloalkyl group, or any two of $R^3$, $R^4$, and $R^5$, for example, $R^3$ and $R^4$ be bonded to each other to form a 5-membered or 6-membered ring, or any two of $R^3$, $R^4$, and $R^5$, for example, $R^3$ and $R^4$ be bonded to each other via an oxygen atom to form a 5-membered or 6-membered ring. The amine compound represented by the above-described Formula (3) may include two or more ring structures.

Specific examples of the amine compound represented by the general formula (3) include, but are not particularly limited to, N,N-dimethylbenzylamine, N,N-diethylbenzylamine, N,N-dibenzylmethylamine, N,N-dimethyl-4-methylbenzylamine, N,N-dimethylcyclohexylamine, N,N-diethylcyclohexylamine, N,N-dicyclohexylmethylamine, N,N-dicyclohexylethylamine, N-methylpyrrolidine, N-ethylpyrrolidine, N-propylpiperidine, N-butylpiperidine, N-methylmorpholine, N-ethylmorpholine, N-propylmorpholine, N-butylmorpholine, N-sec-butylmorpholine, N-tert-butylmorpholine, N-isobutylmorpholine, N,N-diisopropylmethylamine, N,N-diisopropylethylamine, N,N-bis(2-hydroxyethyl)benzylamine, and N-methyl diphenylamine. Particularly preferred are N,N-dimethylcyclohexylamine, N-methylpiperidine and N-ethylmorpholine in view of solubility and storage stability.

The ratio of the molecular weight of the arylsulfonic acid/the molecular weight of the tertiary amine compound is preferably 0.8 to 2.0, and more preferably 1.3 to 2.0. In a case where the ratio of the molecular weight of the arylsulfonic acid/the molecular weight of the tertiary amine compound is 0.8 or less, that is, in a case where the molecular weight of the tertiary amine is too large, the weight parts of the sulfo group per unit weight of the arylsulfonic acid amine salt is small, and excessive oil solubility may thus be provided to thereby impair the amphiphilicity. In a case where the ratio of the molecular weight of the arylsulfonic acid/the molecular weight of the tertiary amine compound is 2.0 or more, that is, in a case where the molecular weight of the tertiary amine is too small, insufficient oil solubility may thus be provided to thereby impair the amphiphilicity.

Arylsulfonic Acid Amine Salt (Co)Polymer

Although a method for producing a high-purity arylsulfonic acid amine salt (co)polymer using the monomer of the high-purity arylsulfonic acid amine salt shown in the present embodiment is not particularly limited, the (co)polymer can be synthesized by a radical polymerization method such as bulk polymerization, solution polymerization, dispersion polymerization, suspension polymerization, or emulsion polymerization.

For example, in the case of solution radical polymerization, the polymerization may be performed by placing, in a reaction vessel, a homogeneous solution of an arbitrary solvent and the arylsulfonic acid amine salt shown in the present embodiment and optionally a comonomer mixture capable of radical copolymerization with an arylsulfonic acid amine salt, optionally adding a molecular weight regulator, deoxidizing the inside of the system by a method such as blowing nitrogen gas or repeating decompression and nitrogen introduction, then heating to a predetermined temperature, and polymerizing while adding radical polymerization initiator. At this time, in order to avoid abrupt polymerization and in consideration of the molecular weight controllability in a low molecular weight region, it is preferable to add each monomer together with the polymerization initiator and the molecular weight regulator in small portions, rather than to place all the monomer mixture in the reaction vessel from the beginning.

The reaction solvent is not particularly limited; the composition thereof is not particularly limited as long as the mixture of the arylsulfonic acid amine salt and the comonomer can be dissolved therein, and the composition of the solvent may be changed as required. Examples thereof include water or water-soluble solvents such as water, acetone, tetrahydrofuran, dioxane, methanol, ethanol, n-propanol, isopropanol, methoxyethanol, ethoxyethanol, butanol, ethylene glycol, propylene glycol, glycerin, dimethyl sulfoxide, dimethylformamide, and N-methylpyrrolidone, linear aliphatic hydrocarbons such as pentane, hexane, cyclohexane, methylcyclohexane, heptane, octane, nonane, decane, undecane, dodecane, tridecane, tetradecane, pentadecane, hexadecane, heptadecane, and octadecane, aromatic hydrocarbons such as benzene, toluene, o-xylene, m-xylene, and p-xylene, and aliphatic halogen compounds such as methylene chloride, chloroform, carbon tetrachloride,1,2-dichloroethane, and a mixture thereof.

From these solvents, the polymerization solvent can be appropriately selected in accordance with the application of the (co)polymer. In view of the polymerization conversion rate, water and alcohols are preferably used alone or as a mixed solvent, and in general, it is preferable that the amount used of the aqueous solvent serving as the reaction solvent be usually 150 parts by weight to 2,000 parts by weight with respect to 100 parts by weight of the total amount of monomers.

Another monomer than the arylsulfonic acid amine salt used for the arylsulfonic acid amine salt (co)polymer of the present invention is not particularly limited as long as the monomer can be radically copolymerized with the arylsulfonic acid amine salt. Examples thereof include maleimides such as N-cyclohexylmaleimide, N-methylmaleimide, N-ethylmaleimide, N-phenylmaleimide, N-(chlorophenyl) maleimide, N-(methylphenyl)maleimide, N-(isopropylphenyl)maleimide, N-(sulfophenyl)maleimide, N-methylphenylmaleimide, N-bromophenylmaleimide, N-naphthylmaleimide, N-hydroxyphenylmaleimide, N-methoxyphenylmaleimide, N-carboxyphenylmaleimide, N-(nitrophenyl)maleimide, N-benzylmaleimide, N-(4-acetoxy-1-naphthyl)maleimide, N-(4-oxy-1-naphthyl)maleimide, N-(3-fluorantil)maleimide, N-(5-fluoresceinyl)maleimide, N-(1-pyrenyl)maleimide, N-(2,3-xylyl)maleimide, N-(2,4-xylyl)maleimide, N-(2,6-xylyl)maleimide, N-(aminophenyl)maleimide, N-(tribromophenyl)maleimide, N-[4-(2-benzimidazolyl)phenyl]maleimide, N-(3,5-dinitrophenyl)maleimide, and N-(9-acridinyl) maleimide; fumaric acid diesters such as dibutyl fumarate, dipropyl fumarate, diethyl fumarate, and dicyclohexyl fumarate; fumaric acid monoesters such as butyl fumarate, propyl fumarate, and ethyl fumarate; maleic diesters such as dibutyl maleate, dipropyl maleate, and diethyl maleate; maleic acid monoesters such as butyl maleate, propyl maleate, ethyl maleate, and dicyclohexyl maleate; acid anhydrides such as maleic anhydride and citraconic anhydride; styrenes such as styrene, chlorostyrene, dichlorostyrene, bromostyrene, dibromostyrene, fluorostyrene, trifluorostyrene, nitrostyrene, cyanostyrene, α-methylstyrene, p-chloromethylstyrene, p-cyanostyrene, p-acetoxystyrene, p-styrenesulfonyl chloride, ethyl p-styrenesulfonyl, methyl p-styrenesulfonyl, propyl p-styrenesulfonyl, p-butoxystyrene, 4-vinylbenzoic acid, and 3-isopropenyl-α,α'-dimethylbenzyl isocyanate; vinyl ethers such as butyl vinyl ether, ethyl vinyl ether, 2-phenyl vinyl alkyl ether, nitrophenyl vinyl ether, cyanophenyl vinyl ether, and chlorophenyl vinyl ether; acrylic acid esters such as methyl acrylate, ethyl acrylate, propyl acrylate, butyl acrylate, pentyl acrylate, hexyl acrylate, decyl acrylate, lauryl acrylate, octyl acrylate, dodecyl acrylate, stearyl acrylate, 2-ethylhexyl acrylate, cyclohexyl acrylate, bornyl acrylate, 2-ethoxyethyl acrylate, 2-butoxyethyl acrylate, 2-hydroxyethyl acrylate, tetrahydrofurfuryl acrylate, methoxyethylene glycol acrylate, ethyl carbitol acrylate, 2-hydroxypropyl acrylate, 4-hydroxybutyl acrylate, 3-(trimethoxysilyl)propyl acrylate, polyethylene glycol acrylate, glycidyl acrylate, 2-(acryloyloxy)ethyl phosphate, 2,2,3,3-tetrafluoropropyl acrylate, 2,2,2-trifluoroethyl acrylate, 2,2,3,3,3-pentafluoropropyl acrylate, and 2,2,3,4,4,4-hexafluorobutyl acrylate; methacrylic acid esters such as methyl methacrylate, t-butyl methacrylate, sec-butyl methacrylate, i-butyl methacrylate, i-propyl methacrylate, decyl methacrylate, lauryl methacrylate, octyl methacrylate, dodecyl methacrylate, stearyl methacrylate, cyclohexyl methacrylate, bornyl methacrylate, benzyl methacrylate, phenyl methacrylate, glycidyl methacrylate, polyethylene glycol methacrylate, 2-hydroxyethyl methacrylate, tetrahydrofurfuryl methacrylate, methoxyethylene glycol methacrylate, ethyl carbitol methacrylate, 2-hydroxypropyl methacrylate, 4-hydroxybutyl methacrylate, 2-(methacryloyloxy) ethyl phosphate, 2-(dimethylamino)ethyl methacrylate, 2-(diethylamino)ethyl methacrylate, 3-(dimethylamino)propyl methacrylate, 2-(isocyanato)ethyl methacrylate, 2,4,6-tribromophenyl methacrylate, 2,2,3,3-tetrafluoropropyl methacrylate, 2,2,2-trifluoroethyl methacrylate, 2,2,3,3,3-pentafluoropropyl methacrylate, and 2,2,3,4,4,4-hexafluorobutyl methacrylate; 1,3-butadienes such as 1,3-butadiene, 2-methyl-1,3-butadiene, 2-chloro-1,3-butadiene, 2,3-dichloro-1,3-butadiene, 2-cyano-1,3-butadiene, 1-chloro-1,3-butadiene, 2-(N-piperidylmethyl)-1,3-butadiene, 2-triethoxymethyl-1,3-butadiene, 2-(N,N-dimethylamino)-1,3-butadiene, N-(2-methylene-3-butenoyl)morpholine, and diethyl 2-methylene-3-butenylphosphonate; and others such as acrylamide, methacrylamide, sulfophenylacrylamide, sulfophenylitaconimide, acrylonitrile, methacrylonitrile, fumaronitrile, vinyl chloride, α-cyanoethyl acrylate, citraconic anhydride, vinyl acetate, vinyl propionate, vinyl pivalate, versamic vinyl acid, acrylic acid, methacrylic acid, crotonic acid, itaconic acid, fumaric acid, mono-2-(methacryloyloxy)ethyl phthalate, mono-2-(methacryloyloxy) ethyl succinate, mono-2-(acryloyloxy)ethyl succinate, methacryloxypropyltrimethoxysilane, methacryloxypropyldimethoxysilane, acrolein, diacetone acrylamide, vinyl methyl ketone, vinyl ethyl ketone, diacetone methacrylate, vinyl sulfonic acid, isoprene sulfonic acid, allyl sulfonic acid, 2-acrylamido-2-methylpropanesulfonic acid, 2-acrylamido-1-methylsulfonic acid, 2-methacrylamide-2-methylpropanesulfonic acid, vinylpyrrolidone, dehydroalanine, sulfur dioxide, isobutene, n-vinylcarbazole, vinylidene cyanide, paraquinodimethane, chlorotrifluoroethylene, tetrafluoroethylene, norbornen, and n-vinylcarbazole.

Among these, styrenes, methacrylic acid, acrylic acid, acrylic acid esters, methacrylic acid esters, and N-substituted maleimides are preferable in view of, for example, copolymerizability with the arylsulfonic acid amine salts, and availability.

Although the molecular weight regulator is not particularly limited, the examples thereof include diisopropyl xanthogen disulfide, diethyl xanthogen disulfide, diethylthiuram disulfide, 2,2'-dithiodipropionic acid, 3,3'-dithiodipropionic acid, 4,4'-dithiodibutanoic acid, and disulfides such as 2,2'-dithiobisbenzoic acid; mercaptans such as n-dodecyl mercaptan, octyl mercaptan, t-butyl mercaptan, thioglycolic acid, thiomalic acid, 2-mercaptopropionic acid, 3-mercaptopropionic acid, thiosalicylic acid, 3-mercaptobenzoic acid, 4-mercaptobenzoic acid, thiomalonic acid, dithiosuccinic acid, thiomaleic acid, thiomaleic anhydride, dithiomaleic acid, thioglutaric acid, cysteine, homocysteine, 5-mercaptotetrazole acetic acid, 3-mercapto-1-propanesulfonic acid, 3-mercaptopropane-1,2-diol, mercaptoethanol, 1,2-dimethylmercaptoethane, 2-mercaptoethylamine hydrochloride, 6-mercapto-1-hexanol, 2-mercapto-1-imidazole, 3-mercapto-1,2,4-triazole, cysteine, N-acylcysteine, glutathione, N-butylaminoethanethiol, and N,N-diethylaminoethanethiol; halogenated hydrocarbons such as iodoform; and diphenylethylene, p-chlorodiphenylethylene, p-cyanodiphenylethylene, α-methylstyrene dimer, benzyldithiobenzoate, 2-cyanoprop-2-yldithiobenzoate, organic tellurium compounds, sulfur, sodium sulfite, potassium sulfite, sodium bisulfite, potassium bisulfite, sodium pyrosulfite, and potassium pyrosulfite.

The amount of the molecular weight regulator used is usually 0.1 to 10 parts by weight with respect to 100 parts by weight of the total amount of monomers.

Examples of the radical polymerization initiator includes peroxides such as di-t-butyl peroxide, dicumyl peroxide, t-butyl cumyl peroxide, benzoyl peroxide, dilauryl peroxide, cumene hydroperoxide, t-butyl hydroperoxide, 1,1-bis(t-butylperoxy)-3,5,5-trimethylcyclohexane, 1,1-bis(t-butylperoxy)-cyclohexane, cyclohexanone peroxide, t-butyl peroxybenzoate, t-butyl peroxyisobutyrate, t-butylperoxy-3,5,5-trimethylhexanoate, t-butylperoxy-2-ethylhexanoate, t-butyl peroxyisopropyl carbonate, cumyl peroxy octoate, potassium persulfate, ammonium persulfate, and hydrogen peroxide; and azo compounds such as 2,2'-azobis(4-methoxy-2,4-dimethylvaleronitrile), 2,2'-azobis(2,4-dimethylvaleronitrile), 2,2'-azobis(2-methylpropionitrile), 2,2'-azobis(2-methylbutyronitrile), 1,1'-azobis(cyclohexane-1-carbonitrile), 1-[(1-cyano-1-methylethyl)azo]formamide, dimethyl 2,2'-azobis(2-methylpropionate), 4,4'-azobis(4-cyanovaleric acid), 2,2'-azobis(2,4,4-trimethylpentane), 2,2'-azobis{2-methyl-N-[1,1'-bis(hydroxymethyl)-2-hydroxyethyl]propionamide}, 2,2'-azobis{2-(2-imidazolin-2-yl)propane]dihydrochloride, 2,2'-azobis{2-(2-imidazolin-2-yl)propane]disulfate dihydrate, 2,2'-azobis{2-[1-(2-hydroxyethyl)-2-imidazolin-2-yl)propane]}dihydrochloride, 2,2'-azobis(1-imino-1-pyrrolidino-2-methylpropane) dihydrochloride, 2,2'-azobis(2-methylpropionamidine) dihydrochloride, and 2,2'-azobis[N-(2-carboxyethyl)-2-methylpropionamidine] tetrahydrate.

The amount of the radical polymerization initiator used is usually 0.1 to 10 parts by weight with respect to 100 parts by weight of the total amount of monomers.

For example, in the case of emulsion radical polymerization, the radically polymerizable monomer described above is mixed with the arylsulfonic acid amine salt of the present invention or an aqueous solution containing the arylsulfonic acid amine salt and an emulsifier, and the mixture is emulsified by stirring or homogenizer treatment to prepare a monomer emulsion. The polymerization may be performed by placing the monomer emulsion in a reactor, degassing the system, and then polymerizing at a predetermined temperature while adding a polymerization initiator. In this case, in order to avoid sudden heat generation, the polymerization may be performed by placing a part of the monomer emulsion the reactor to start polymerization, and then polymerizing while continuously adding the remaining monomer emulsion. Alternatively, the polymerization may be performed by continuously adding a radically polymerizable monomer into a solution including an emulsifier. The radically polymerizable monomer, the reaction solvent, the radical polymerization initiator, and the molecular weight regulator in the emulsion radical polymerization are not particularly limited, and examples thereof that may be used include the compounds for the solution radical polymerization described above.

Since the arylsulfonic acid amine salt of the present invention is a reactive emulsifier having a high emulsifying power, an emulsifier is not always necessary in the emulsion polymerization, but there are cases where the emulsion is stabilized by using an additional emulsifier in combination. Although the emulsifier that may be used in this case is not particularly limited, examples of anionic emulsifiers include rosin acid salts, fatty acid salts, alkenyl succinic acid salts, alkyl ether carboxylic acid salts, alkyl diphenyl ether disulfonic acid salts, alkane sulfonic acid salts, alkyl succinate sulfonic acid salts, polyoxyethylene polycyclic phenyl ether sulfonic acid ester salts, α-olefin sulfonic acid salts, alkylbenzene sulfonic acid salts, naphthalene sulfonate formalin condensates, taurine derivatives, polystyrenesulfonic acids, polystyrenesulfonic acid styrene copolymers, polystyrenesulfonic acid N-vinylpyrrolide copolymers, polystyrenesulfonic acid N-substituted maleimide copolymers, polystyrenesulfonic acid methacrylic acid copolymers, polystyrenesulfonic acid acrylic acid copolymers, polystyrenesulfonic acid acrylic acid ester copolymers, styrenesulfonic acid maleic acid copolymers, styrenesulfonic acid acrylamide copolymers, styrenesulfonic acid methacrylamide copolymers, styrenesulfonic acid 2-hydroxyethyl methacrylate copolymers, polyvinyl phosphonic acid copolymers, polyvinyl sulfonic acid copolymers, polyisoprene sulfonic acid copolymers, polyacrylic acid ester acrylic acid copolymers, polymethacrylic acid ester methacrylic acid copolymers, polyacrylamide acrylic acid copolymers, polymethacrylamide methacrylic acid copolymers, alkylsulfosuccinic acid salts, alkyl sulfuric acid salts, alkyl ether sulfuric acid salts, sulfuric acid ester salts of alkyl propenyl phenol polyethylene oxide adduct, sulfuric acid ester salts of allyl alkylphenol polyethylene oxide adduct, alkyl phosphate salts, polyoxyethylene alkyl ether phosphoric acid ester salt, sulfonic acid salts of higher fatty acid amides, and sulfuric acid salts of higher fatty acid alkylolamides, examples of nonionic emulsifiers include polyoxyalkylene alkylamine, alkyl alkanolamide, amine oxide nonionic emulsifier, polyoxyethylene alkyl ether, polyoxyethylene alkyl phenyl ether, polyoxyalkylene polycyclic phenyl ether, alkyl propenylphenol polyethylene oxide adducts, allyl alkylphenol polyethylene oxide adducts, polyoxyethylene fatty acid esters, polyoxyethylene sorbitan fatty acid esters, sorbitan fatty acid esters, glycerin fatty acid esters, alkyl polyglucooxides, sucrose fatty acid esters, polyoxyethylene polyoxypropylene glycol, polyvinyl alcohol, carboxymethylcellulose, polyvinylpyrrolidone, hydroxyethyl cellulose, polyacrylamide, polymethacrylamide, polydimethylaminoethyl methacrylate, polydimethylaminoethyl acrylate, polydiethylaminoethyl methacrylate, polydiethylaminoethyl acrylate, poly-t-butylethylaminoethyl methacrylate, poly-t-butylaminoethyl acrylate, polydimethylaminoethyl methacrylate/methyl methacrylate copolymer, polydimethylaminoethyl acrylate/methyl methacrylate copolymer, polydimethylaminoethyl methacrylate/butyl acrylate copolymer, and polydimethylaminoethyl acrylate/ethyl acrylate copolymer, and examples of amphoteric emulsifiers include alkyldimethylaminoacetic acid betaines, alkyldimethylaminosulfobetaines, and alkylsulfobetaines.

The arylsulfonic acid amine salt polymer obtained by polymerizing the arylsulfonic acid amine salt according to the present invention as described above has a molecular weight of, for example, about 1,000 to 5,000,000 daltons (Da) in terms of a number average molecular weight measured by gel permeation chromatography (GPC).

This polymer is a polymer of arylsulfonic acid amine salt obtained by dissolving the arylsulfonic acid amine salt in an arbitrary solvent to obtain a mixture, optionally adding and dissolving a molecular weight regulator and/or an emulsifier into the mixture, adding a radical polymerization initiator into the mixture under a nitrogen atmosphere, and reacting the mixture with heating and stirring. The detailed material properties of the polymer, e.g. the chemical structure, are difficult to analyze, and such material properties are more easily understood by describing the producing method, as an alternative.

As the solvent that may be used when the arylsulfonic acid amine salt, the emulsifier, the molecular weight regulator, and the solvent are mixed and dissolved, various solvents such as water, an aqueous solvent or a solvent capable of dissolving the arylsulfonic acid amine salt (monomer) may be used.

EXAMPLES

The following Examples further illustrate the present invention, but it should be noted that the present invention is not limited by these Examples in anyway.

Identification of Target Product and Determination of Purity by Nuclear Magnetic Resonance Spectrum (1) Sample Preparation Samples were dissolved in about 0.7 mL of dimethyl sulfoxide-d6 (99.5 weight %) or chloroform-d (99.5 wt %) containing about 0.05 wt % tetramethylsilane that serves as an internal standard to prepare the samples for NMR measurement.

(2) Measuring Equipment
Model=Bruker AV-400M
Number of scans=16

(3) Calculation of Purity

The purity of the product was calculated by the following equation.

$$\text{Purity (wt \%)} = (B/M_b) \times (a/a_H)/(b/b_H) \times M_a/S \times 100$$

a: integral of arbitrary target product peak
b: integral of arbitrary internal standard
$a_H$: number of hydrogen atoms indicated by arbitrary product peak selected for a
$b_H$: number of hydrogen atoms indicated by arbitrary product peak selected for b
$M_a$: molecular weight of target product
$M_b$: molecular weight of internal standard
B: amount of internal standard collected (g)
S: amount of sample collected (g)

Analysis of Polymer by Gel Permeation Chromatography (GPC)

The polymer was quantified (area %) using HLC-8320 manufactured by Tosoh Corporation. A sample was dissolved in water or acetonitrile or a mixed solvent thereof to prepare a 0.1 wt % solution, and GPC measurement was performed thereon under the following conditions. From a peak area (a) derived from monomer and a peak area (b) derived from polymer, the polymer content was calculated by the following Equation.

$$\text{Polymer content (area \%)} = 100 \times a/(a+b)$$

Column=TSK AW6000+AW3000+TSK Guard column AW-H
Eluent=sodium sulfate aqueous solution (0.05 mol/L)/acetonitrile=65/35 (Vol ratio) solution
Or sodium sulfate aqueous solution (0.05 mol/L)/acetonitrile=90/10 (Vol ratio) solution
Or lithium bromide dimethylformamide solution (10 mmol/L)
Flow rate/injection volume/column temperature=0.6 ml/min, injection volume=10 µl, column temperature=40° C.
Detector=UV detector (wavelength 230 nm)
Calibration curve=standard polystyrene sulfonate sodium (manufactured by Sowa Science)

Quantification of Residual Monomer Amount by Gas Chromatography (GC)

In the analysis of the polymerization conversion rate, the residual amount of monomer was quantified using GC-14A manufactured by Shimadzu Corporation together with the analysis by GPC. The analysis was performed under the following conditions by injecting 0.2 µl of the sample solution with a microsyringe. Further, the calibration curve of internal standard concentration vs peak area % was prepared using an internal standard, and then the monomer content was calculated from the peak area derived from monomer and the peak area derived from internal standard. In the case of styrene, the retention time (rt) was 17.5 min under the following conditions.
Detector=FID, carrier gas: He
Column=PEG20M Chromosorb WAW 15% 80-100 mesh
Detector temperature: 190° C., INJ temperature: 200° C.
Column temperature: 60° C.-190° C. (5° C./min)
Internal standard: n-BuOH (rt=13.2 min)

Example 1

Synthesis Example of Parastyrenesulfonic Acid N,N-Dimethylcyclohexylamine Salt 40.0 g of N,N-dimethylcyclohexylamine (manufactured by Tokyo Chemical Industry Co., Ltd.) was placed in a 200 mL glass four-necked flask equipped with a reflux condenser, a nitrogen inlet tube, and a dropping funnel. The N,N-dimethylcyclohexylamine was cooled to 0° C., and under continuous cooling, a mixed solution of 33.0 g of 35% hydrochloric acid (manufactured by Wako Pure Chemical Industries, Ltd.) and 30.0 g of deionized water was added dropwise thereto. After completion of the dropwise addition, the mixture was stirred at room temperature for 1 hour to obtain an aqueous solution of N,N-dimethylcyclohexylamine hydrochloride.

Next, 72.8 g of sodium parastyrenesulfonate (manufactured by Tosoh Organic Chemical Co., Ltd.) and 330 g of deionized water were placed in a 1000 mL glass four-necked flask equipped with a reflux condenser, a nitrogen inlet tube, and a dropping pipe funnel, and the mixture was stirred and dissolved at the room temperature. Into the solution, 103 g of the dimethylcyclohexylamine hydrochloride aqueous solution synthesized earlier was added dropwise over 1 hour, and after completion of the addition, the solution was stirred at room temperature for 1 hour. After completion of the reaction, the reaction solution (aqueous layer) was extracted twice with 200 g of chloroform, and the chloroform was distilled off with an evaporator, whereby a yield of 80.4 g of a white solid of parastyrenesulfonic acid N,N-dimethylcyclohexylamine salt was obtained (yield 82.1%, purity 99.8%).

The target product was identified by proton NMR ($^1$H-NMR). Elemental analysis of the target product for carbon (C), hydrogen (H), and nitrogen (N) was conducted using an element analyzer, and that for sulfur (S) was conducted using an oxygen flask combustion method, in which after carrying out a combustion absorption treatment, $SO_4^{2-}$ ion is quantified by ion chromatography and the found value is converted in terms of sulfur (S). Table 1 shows the results of elemental analysis.

Result of Analysis

1) $^1$H-NMR (400 MHz, CDCl3): δ 10.6 (1H, s), δ 7.84 (2H, d), δ 7.41 (2H, d), δ 6.71 (1H, dd), δ 5.78 (1H, d), δ 5.29 (1H, d), δ 3.06 (1H, ddd), δ 2.80 (6H, s), δ 2.12 (2H, d), δ 1.91 (2H, d), δ 1.70 (1H, d), δ 1.44-1.25 (4H, m), δ 1.19-1.08 (1H, m)

2) Elemental Analysis:

TABLE 1

|  | C(%) | H(%) | N(%) | S(%) |
| --- | --- | --- | --- | --- |
| Calculated | 61.7 | 8.1 | 4.5 | 10.29 |
| Measured | 61.1 | 8.2 | 4.5 | 9.8 |

Example 2

Synthesis Example of Parastyrenesulfonic Acid N,N-Dimethylcyclohexylamine Salt 10.0 g of a 70% aqueous solution of 4-(2-bromoethyl)benzenesulfonic acid (manufactured by Tosoh Organic Chemical Co., Ltd.), 12.5 g of N,N-dimethylcyclohexylamine, and 27 mg of hydroquinone (manufactured by Wako Pure Chemical Industries, Ltd.) were placed in a 100 mL four-necked glass flask equipped with a reflux condenser, a nitrogen inlet tube, and a dropping funnel. The mixed solution was heated to 90° C. and left to stir for 2 hours. After completion of the reaction, the reaction solution was cooled to room temperature, and the precipitated crude crystals were filtered, and rinsed twice with toluene 10 g, and dried under reduced pressure, whereby a yield of 6.04 g of a white solid of parastyrenesulfonic acid N,N-dimethylcyclohexylamine salt was obtained (yield 78.4%, purity 98.2%).

The target product was identified by proton NMR ($^1$H-NMR).

Example 3

Synthesis Example of Parastyrenesulfonic Acid N,N-Diisopropylethylamine Salt 10.0 g of N,N-diisopropylethylamine (manufactured by Tokyo Chemical Industry Co., Ltd.) was placed in a 100 mL glass four-necked flask equipped with a reflux condenser, a nitrogen inlet tube, and a dropping funnel. The N,N-dimethylcyclohexylamine was cooled to 0° C., and under continuous cooling, a mixed solution of 7.5 g of 35% hydrochloric acid (manufactured by Wako Pure Chemical Industries, Ltd.) and 10.0 g of deionized water was added dropwise thereto. After completion of the dropwise addition, the mixture was stirred at room temperature for 1 hour to obtain an aqueous solution of N,N-diisopropylethylamine hydrochloride.

Next, 18.2 g of sodium parastyrenesulfonate (manufactured by Tosoh Organic Chemical Co., Ltd.) and 100 g of deionized water were placed in a 300 mL glass four-necked flask equipped with a reflux condenser, a nitrogen inlet tube, and a dropping funnel, and the mixture was stirred and dissolved at the room temperature. Into the solution, 27.5 g of the N,N-diisopropylethylamine hydrochloride aqueous solution synthesized earlier was added dropwise over 1 hour, and after completion of the dropwise addition, the solution was stirred at room temperature for 1 hour. After completion of the reaction, the reaction solution (aqueous layer) was extracted twice with 100 g of chloroform, and the chloroform was distilled off with an evaporator, whereby a yield of 16.2 g of a white solid of parastyrenesulfonic acid N,N-diisopropylethylamine salt was obtained (yield 65.8%, purity 99.2%).

The target product was identified by proton NMR ($^1$H-NMR).

Result of Analysis $^1$H-NMR (400 MHz, CDCl3): δ 9.52 (1H, s), δ 7.78 (2H, d), δ 7.33 (2H, d), δ 6.64 (1H, dd), δ 5.70 (1H, d), δ 5.21 (1H, d), δ 3.61 (2H, m), δ 3.03 (2H, q), δ 1.40-1.32 (15H, m)

Example 4

Synthesis Example of Poly(Parastyrenesulfonic Acid N,N-Dimethylcyclohexylamine Salt)

1.5 g of the parastyrenesulfonic acid N,N-dimethylcyclohexylamine salt obtained in Example 1 and 13.5 g of deionized water were placed in a 100 mL glass four-necked flask, and the mixture was stirred and dissolved at room temperature. The solution was sufficiently degassed by repeating aspirator decompression and nitrogen introduction, and 0.013 g of 2,2'-azobis(2-methylpropionamidine) dihydrochloride (manufactured by Wako Pure Chemical Industries, Ltd.) was added thereto while blowing nitrogen. The solution was heated and stirred at 60° C. for 6 hours to obtain a transparent homogeneous aqueous solution of poly(parastyrenesulfonic acid N,N-dimethylcyclohexylamine salt). The polymerization conversion rate at the end of the reaction was 100%, and the number average molecular weight was 150,000.

The polymerization conversion rate and the number average molecular weight were calculated from the peak area ratio by gel permeation chromatography (GPC).

Example 5

Example of Emulsion Polymerization of Styrene Using Parastyrenesulfonic Acid N,N-Dimethylcyclohexylamine Salt 10.0 g of styrene (manufactured by Wako Pure Chemical Industries, Ltd.), 0.31 g of the parastyrenesulfonic acid N,N-dimethylcyclohexylamine salt obtained in Example 1, 0.25 g of sodium dodecylbenzenesulfonate (manufactured by Wako Pure Chemical Industries, Ltd.), and 20.5 g of deionized water were placed in a 100 mL glass four-necked flask, and the mixture was stirred and dissolved at room temperature. The solution was sufficiently degassed by repeating aspirator decompression and nitrogen introduction, and 0.025 g of 2,2'-azobis(2-methylpropionamidine) dihydrochloride (manufactured by Wako Pure Chemical Industries, Ltd.) was added thereto while blowing nitrogen. The solution was heated and stirred at 60° C. for 24 hours to obtain an emulsion polymerization solution of styrene. The polymerization conversion rate at the end of the reaction was 100%, and the number average molecular weight was 200,000.

The polymerization conversion rate was calculated using the residual amount of monomer measured by gas chromatography, and the number average molecular weight was calculated by gel permeation chromatography (GPC).

Example 6

Synthesis Example of Divinylbenzenesulfonic Acid N,N-Dimethylcyclohexylamine Salt 40.0 g of N,N-dimethylcyclohexylamine was placed in a 200 mL glass four-necked flask equipped with a reflux condenser, a nitrogen inlet tube, and a dropping funnel. The N,N-dimethylcyclohexylamine was cooled to 0° C., and under continuous cooling, a mixed solution of 33.0 g of 35% hydrochloric acid (manufactured by Wako Pure Chemical Industries, Ltd.) and 30.0 g of deionized water was added dropwise thereto. After completion of the dropwise addition, the mixture was stirred at room temperature for 1 hour to obtain an aqueous solution of N,N-dimethylcyclohexylamine hydrochloride.

Next, 7.9 g of sodium divinylbenzenesulfonate (manufactured by Tosoh Organic Chemical Co., Ltd.) and 158 g of deionized water were placed in a 1000 mL glass four-necked flask equipped with a reflux condenser, a nitrogen inlet tube, and a dropping pipe, and the mixture was stirred and dissolved at the room temperature. Into the solution, 103 g of the dimethylcyclohexylamine hydrochloride aqueous solution synthesized earlier was added dropwise over 1 hour, and after completion of the dropwise addition, the solution was stirred at room temperature for 1 hour. After completion of the reaction, the reaction solution (aqueous layer) was extracted twice with 200 g of chloroform, and the chloroform was distilled off with an evaporator, whereby a yield of 7.3 g of a white solid of divinylbenzenesulfonic acid N,N-dimethylcyclohexylamine salt was obtained (yield 71.5%, purity 98.0%).

The target product was identified by proton NMR ($^1$H-NMR).

Comparative Example 1

Synthesis Example of Parastyrenesulfonic Acid n-Trioctylamine Salt 10.0 g of n-trioctylamine (manufactured by Tokyo Chemical Industry Co., Ltd.) and 40 g of n-hexane were placed in a 100 mL glass four-necked flask equipped with a reflux condenser, a nitrogen inlet tube, and a dropping funnel, and the mixture was stirred and dissolved. The solution was cooled to 0° C., and under continuous cooling, 3.2 g of 35% hydrochloric acid (manufactured by Wako Pure Chemical Industries) was added dropwise thereto. After completion of the dropwise addition, the mixture was stirred at room temperature for 1 hour. After completion of the reaction, the precipitated n-trioctylamine hydrochloride was filtered and dried under reduced pressure.

Next, 2.2 g of sodium parastyrenesulfonate and 20 g of deionized water were placed in a 100 mL glass four-necked flask equipped with a reflux condenser, a nitrogen inlet tube, and a dropping funnel, and the mixture was stirred and dissolved at the room temperature. Into the solution, a solution prepared from 3.6 g of n-trioctylamine hydrochloride obtained above and 32 g of dichloromethane was added dropwise over 1 hour, and after completion of the dropwise addition, the solution was stirred at room temperature for 1 hour. After completion of the reaction, 20 g of dichloromethane was added to the reaction solution, and the mixture was separated, and then the organic layer was distilled off, whereby a yield of 4.54 g of a white solid of parastyrenesulfonic acid n-trioctylamine salt was obtained (yield 77.4%, purity 98.4%).

The target product was identified by proton NMR ($^1$H-NMR).

Result of Analysis $^1$H-NMR (400 MHz, DMSO-d6): δ 8.96 (1H, s), δ 7.59 (1H, d), δ 7.42 (2H, d), δ 6.72 (1H, dd), δ 5.84 (1H, d), δ 5.28 (1H, d), δ 3.01 (6H, t), δ 1.59-1.56 (6H, m), δ 1.29-1.23 (30H, m), δ 0.86 (9H, t)

Comparative Example 2

Synthesis Example of Parastyrenesulfonic Acid n-Monoctylamine Salt 12.9 g of n-monoctylamine (manufactured by Tokyo Chemical Industry Co., Ltd.) and 70.5 g of deionized water were placed in a 200 mL glass four-necked flask equipped with a reflux condenser, a nitrogen inlet tube, and a dropping funnel. The solution was cooled to 0° C., and under continuous cooling, 10.4 g of 35% hydrochloric acid was added dropwise thereto. After completion of the dropwise addition, the mixture was stirred at room temperature for 1 hour to obtain an aqueous solution of n-monooctylamine hydrochloride.

Next, 23.0 g of sodium parastyrenesulfonate and 87.5 g of deionized water were placed in a 300 mL glass four-necked flask equipped with a reflux condenser, a nitrogen inlet tube, and a dropping funnel, and the mixture was stirred and dissolved at the room temperature. Into the solution, 93.8 g of the n-monooctylamine hydrochloride aqueous solution synthesized earlier was added dropwise over 1 hour, and after completion of the dropwise addition, the solution was stirred at room temperature for 1 hour. After completion of the reaction, the reaction solution was cooled to 5° C., the precipitated crude crystals were filtered, rinsed twice with toluene 100 g, and dried under reduced pressure, whereby a yield of 7.10 g of a white solid of parastyrenesulfonic acid n-monooctylamine salt was obtained (yield 70.5%, purity 96.4%).

The target product was identified by proton NMR ($^1$H-NMR).

Result of Analysis $^1$H-NMR (400 MHz, DMSO-d6): δ 7.68 (2H, s), δ 7.58 (2H, d), δ 7.45 (2H, d), δ 6.73 (1H, dd), δ 5.85 (1H, d), δ 5.28 (1H, d), δ 2.75 (2H, t), δ 1.52-1.47 (2H, m), δ 1.27-1.23 (10H, m), δ 0.86 (3H, t)

Comparative Example 3

Synthesis Example of Parastyrenesulfonic Acid Dicyclohexylamine Salt 10.0 g of dicyclohexylamine (manufactured by Tokyo Chemical Industry Co., Ltd.) and 40 g of n-hexane were placed in a 100 mL glass four-necked flask equipped with a reflux condenser, a nitrogen inlet tube, and a dropping funnel, and the mixture was stirred and dissolved. The solution was cooled to 0° C., and under continuous cooling, 5.6 g of 35% hydrochloric acid (manufactured by Wako Pure Chemical Industries) was added dropwise thereto. After completion of the dropwise addition, the mixture was stirred at room temperature for 1 hour. After completion of the reaction, the precipitated dicyclohexylamine hydrochloride was filtered and dried under reduced pressure.

Next, 6.40 g of sodium parastyrenesulfonate and 100 g of deionized water were placed in a 300 mL glass four-necked flask equipped with a reflux condenser, a nitrogen inlet tube, and a dropping pipe, and the mixture was stirred and dissolved at the room temperature. Into the solution, a solution prepared from 5.9 g of dicyclohexylamine hydrochloride obtained above and 80 g of dichloromethane was added dropwise over 1 hour, and after completion of the dropwise addition, the solution was stirred at room temperature for 1 hour. After completion of the reaction, 80 g of dichloromethane was added to the reaction solution, and the mixture was separated, and then the organic layer was distilled off, whereby a yield of 6.53 g of a white solid of parastyrenesulfonic acid dicyclohexylamine salt was obtained (yield 65.2%, purity 95.4%).

The target product was identified by proton NMR ($^1$H-NMR).

Result of Analysis $^1$H-NMR (400 MHz, DMSO-d6): δ 8.19 (1H, s), δ 7.58 (2H, d), δ 7.45 (2H, d), δ 6.64 (1H, dd), δ 5.85 (1H, d), δ 5.28 (1H, d), δ 3.09 (2H, m), δ 1.98 (4H, m), δ 1.73 (4H, m), δ 1.62-1.59 (2H, m), δ 1.28-1.23 (8H, m), δ 1.10-1.06 (2H, m)

Comparative Example 4

Example of Emulsion Polymerization of Styrene Using Parastyrenesulfonic Acid n-Trioctylamine Salt 10.0 g of styrene (manufactured by Wako Pure Chemical Industries, Ltd.), 0.54 g of the parastyrenesulfonic acid n-trioctylamine salt obtained in Example 1, 0.25 g of sodium dodecylbenzenesulfonate (manufactured by Wako Pure Chemical Industries, Ltd.), and 20.5 g of deionized water were placed in a 100 mL glass four-necked flask, and the mixture was stirred and dissolved at room temperature. The solution was sufficiently degassed by repeating aspirator decompression and nitrogen introduction, and 0.025 g of 2,2'-azobis(2-methylpropionamidine) dihydrochloride was added thereto while blowing nitrogen. The solution was heated and stirred at 60° C. for 24 hours to obtain an emulsion polymerization solution of styrene. The polymerization conversion rate at the end of the reaction was 30%, indicating that a large amount of monomer remained. Further the number average molecular weight thereof was 50,000.

The polymerization conversion rate was calculated using the residual amount of monomer by gas chromatography. The number average molecular weight was calculated by gel permeation chromatography (GPC). Since the polymer was insoluble in water, the polymer was converted to a sodium salt with a 48% aqueous solution of sodium hydroxide in an amount of 5 times by weight based on the reaction solution, and then analyzed by GPC.

Various Evaluations

Evaluation was performed on the parastyrenesulfonic acid amine salts obtained in Examples 1 and 3 and Comparative Examples 1, 2, and 3 as well as a commercially available parastyrenesulfonate sodium (manufactured by Tosoh Organic Chemical Co., Ltd.) as follows. In the following evaluation, the following abbreviations may be used: parastyrenesulfonic acid N,N-dimethylcyclohexylamine salt (CHASS), parastyrenesulfonic acid N,N-diisopropylethylamine salt (DIPEASS), parastyrenesulfonic acid n-trioctylamine (TOASS), parastyrenesulfonic acid n-monooctylamine salt (MOASS), parastyrenesulfonic acid dicyclohexylamine salt (DCHASS), and parastyrenesulfonic acid sodium salt (NaSS).

Evaluation 1 (Solubility)

2 g each of water, tetrahydrofuran (THF), N-methylpyrrolidone (NMP), and toluene were added to glass screw tube bottles. Small portions of styrenesulfonic acid salts were added thereto at 25° C., and the solubilities thereof were observed while shaking the bottles by hand. In each case, the point at which the solid started to remain was determined to be saturation solubility, and the solubility was calculated by the following Equation. The results of solubility are shown in Table 2.

$$\text{Solubility (wt \%)} = A/(S+A) \times 100$$

A: Weight of amine added (g)

S: Weight of solvent (g)

Comparative Example 2, which is a primary amine, and Comparative Example 3, which is a secondary amine, did not have sufficient solubility. Further, the number of carbon atoms of the amine skeletons in Examples 1, which uses a tertiary amine including a cyclic skeleton, and that in Example 2, which uses a tertiary amine containing a tertiary carbon, were one-third that of Comparative Example 1; however, the amine salts of Example 1 and Example 2 were found to have sufficient solubility in an organic solvent and confirmed to be soluble in water and thus to be amphiphilic.

TABLE 2

|  |  | Amine skeleton | | | | Solubility | | | |
| --- | --- | --- | --- | --- | --- | --- | --- | --- | --- |
|  |  | Number of substituents | Number of carbon atoms | Cyclic structure | Tertiary carbon | Water | THF | NMP | Toluene |
| Example 1 | CHASS | 3 | 8 | Yes | Yes | ○ | ○ | ○ | Δ |
| Example 3 | DIPEASS | 3 | 8 | No | Yes | ○ | Δ | ○ | Δ |
| Comparative Example 1 | TOASS | 3 | 24 | No | No | x | ○ | ○ | ○ |
| Comparative Example 2 | MOASS | 1 | 8 | No | No | x | x | ○ | x |
| Comparative Example 3 | DCHASS | 2 | 16 | Yes | Yes | x | x | ○ | x |
| — | NaSS | — | — | — | — | ○ | x | x | x |

○: Easily soluble (10 wt % or more)
Δ: Soluble (1 to 10 wt %)
x: Insoluble (1 wt % or less)

Evaluation 2 (Storage Stability)

2.0 g of the solid of styrenesulfonic acid salt was added to glass screw tube bottle, and the bottle was sealed with a plug. Then, the bottle was placed in a box dryer at 60° C., and an accelerated test of polymerization stability was performed.

Sampling was performed every other day for a total of one week to check properties, odor, pH change, and the progress of polymerization by heat.

The pH was measured using a handy pH meter (manufactured by Mettler Toledo Co., Ltd.) for CHASS and DIPEASS in the form of a 5 wt % aqueous solution and for TOASS and MOASS in the form of a 5 wt % dimethyl sulfoxide solution.

Regarding the polymerization stability, GPC analysis was performed under the same conditions as in the Examples, and the changes over time in the area % of the monomer and polymer were observed.

Table 3 shows the storage stability results before the start of the reaction and after one week.

Comparative Example 1 became a yellow translucent plastic form on the first day of evaluation, and it was clear that polymerization had progressed. TOASS was dissolved in dimethylformamide and subjected to GPC analysis using a 10 mmol/L lithium bromide dimethylformamide solution as eluent.

TABLE 3

|  |  |  | Before start of reaction | | | After one week | | |
| --- | --- | --- | --- | --- | --- | --- | --- | --- |
|  |  | Comprehensive Evaluation | Properties | Odor | Monomer (area %) | Properties | Odor | Monomer (area %) |
| Example 1 | CHASS | ○ | White solid | No | 100 | Slightly yellowish white solid | No | 97.24 |
| Example 3 | DIPEASS | ○ |  |  |  | Yellow solid | No | 92.40 |
| Comparative Example 1 | TOASS | x |  |  |  | Yellow plastic form | Yes | 0.00 |
| Comparative Example 2 | MOASS | ○ |  |  |  | Slightly yellowish white solid | No | 92.20 |

Good: The properties are almost unchanged after one week, and the monomer ratio (polymerization stability) measured by GPC is 90 area % or more.
Poor: The properties of polymer are changed to a plastic form after one week to cause difficulties for measurement.

From the results of Evaluation 1 and Evaluation 2, it has become apparent that arylsulfonic acid amine salts obtained by using, among amines having the same number of carbon atoms, an amine that is a tertiary amine and has a cyclic structure or a tertiary carbon or quaternary carbon in the amine skeleton have excellent solubility and storage stability.

INDUSTRIAL APPLICABILITY

The arylsulfonic acid amine salt vinyl monomer of the present invention is an arylsulfonic acid compound having high purity, high storage stability, and amphiphilic properties, which is extremely useful industrially as a versatile or functional polymer raw material, allowing arylsulfonic acids to be easily applicable to applications that require lipophilicity, such as prevention of static electricity of resins and rubbers and graft polymerization to polyolefins, and realizing further increase of production efficiency compared to conventional water-soluble sulfonic acid monomers even in applications that requires a certain degree of water solubility, such as a reactive emulsifier for emulsion polymerization.

The invention claimed is:

1. An arylsulfonic acid amine salt which is a salt of: an arylsulfonic acid represented by Formula (1):

[Formula 1]

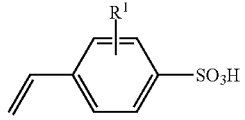

(1)

wherein $R^1$ is a hydrogen
and N,N-dimethylcyclohexylamine.

* * * * *